United States Patent [19]

Rosenberg et al.

[11] Patent Number: 4,687,746

[45] Date of Patent: Aug. 18, 1987

[54] MICROORGANISM CULTURE-TRANSFER DEVICE

[75] Inventors: Melvyn Rosenberg, Ramat-Gan; Ervin Weiss, Tel-Aviv, both of Israel

[73] Assignee: Ramot University Authority for Applied Research and Industrial Development Ltd., Tel Aviv, Israel

[21] Appl. No.: 690,999

[22] Filed: Jan. 14, 1985

[30] Foreign Application Priority Data

Jan. 20, 1984 [IL] Israel ........................................ 70737

[51] Int. Cl.$^4$ .............................................. C12M 1/26
[52] U.S. Cl. .................................... 435/292; 128/759; 422/100
[58] Field of Search ....................... 435/292, 294, 295; 81/177.1, 177.3; 128/757, 756, 759, 304; 73/864.72; 422/68, 100

[56] References Cited

U.S. PATENT DOCUMENTS

| | | | |
|---|---|---|---|
| 3,077,780 | 2/1963 | Takatsy | 73/864.72 |
| 3,173,462 | 3/1965 | Koeppel | 81/177.1 X |
| 3,191,813 | 6/1905 | Duff | 73/864.72 |
| 3,252,331 | 5/1966 | Lancaster | 73/864.72 |
| 3,485,236 | 12/1969 | Frost | 435/292 X |
| 4,010,077 | 3/1977 | Pardos | 435/294 |

*Primary Examiner*—Alan Cohan
*Attorney, Agent, or Firm*—Benjamin J. Barish

[57] ABSTRACT

Microorganism culture transfer devices are described of the type comprising a manually-grippable handle having a culture contacting tip for contacting a culture and streaking same a plurality of times over a culture plate in order to dilute the culture for purposes of isolating individual colonies. The handle is of a configuration in cross-section defining at least three, preferably four or more, discrete rotational positions when held and rotated by the user's fingers about the longitudinal axis of the handle; and the culture-contacting tip is of a configuration such as to provide a different and distinct surface for contact with the culture in each of the discrete rotational positions of the handle.

9 Claims, 12 Drawing Figures

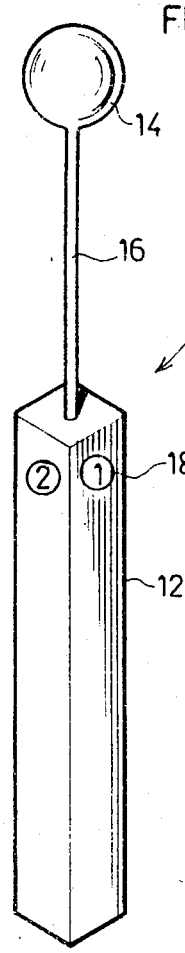
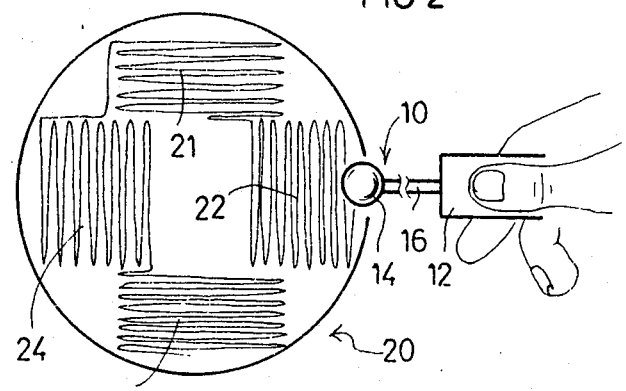
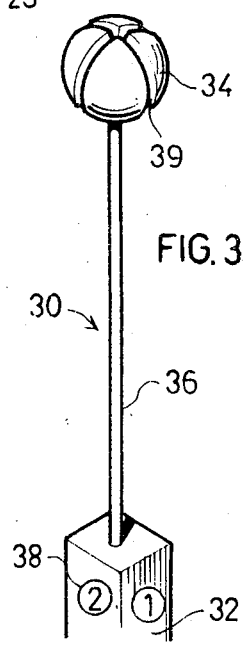
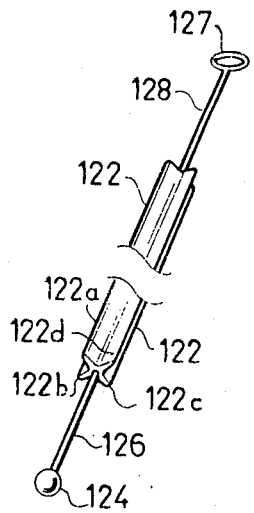
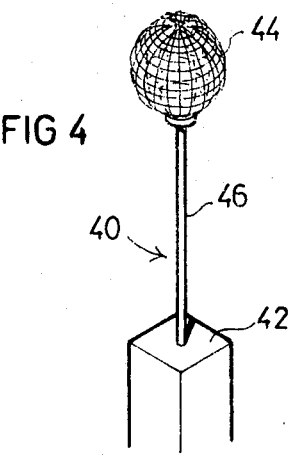
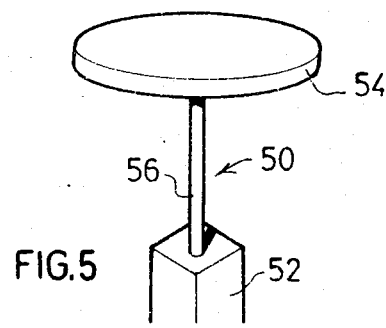

MICROORGANISM CULTURE-TRANSFER DEVICE

BACKGROUND OF THE INVENTION

This invention pertains to the general field of microbiology, and more specifically to a microorganism culture-transfer device for transferring microorganisms to and from solid media for the purpose of obtaining individual colonies.

Most microbiological laboratories must maintain pure cultures of microorganisms for reference and research. In order to maintain strains of individual microorganisms, the cultures are usually streaked onto plates containing solidified medium. The inoculum of the culture is generally from a single colony on a previously inoculated plate, and the aim of the streaking procedure is to obtain individual colonies of the strain on the fresh plate. Individual colonies of identical form signify to the worker that a single cell type has been transferred; moreover a single colony serves as the inoculum for further strain transfer and experimentation. The transfer technique is generally performed at present with a loop at the end of a long handle. The traditional loop is formed from metal (e.g. platinum or nickel-chromium) which can be quickly heat sterilized (e.g. by flame) and quickly cooled by touching the sterile surface of the fresh medium. Recently, sterile, plastic single-use, disposable loops have been introduced.

In the classic technique, known as streaking, the sterile loop is first brought into contact with the colony whose cells one wishes to transfer; it is then brought into contact with the plate containing sterile solid medium to which one wishes to transfer the cells, and is moved back and forth over the surface of a portion (e.g. one quarter) of the fresh plate. In the initial step, millions of cells may be transferred to the new plate, and must be further diluted by many orders of magnitude so that individual colonies, rather than confluent growth, will be obtained. Since the loop surface is also now contaminated with many thousands of cells, it must be either resterilized (e.g., by flame sterilization in the case of wire loops), or substituted by a new sterile loop (e.g. in the case of single-use, disposable plastic loops). The sterile loop is then brought into contact with the surface of the fresh plate which has been previously streaked, e.g. by several movements across the zone of the first streaking, and then another portion of the plate (e.g. a quarter of the plate adjacent to the first streaking) is streaked. This results in additional dilution of the cells. The loop is then either resterilized or replaced, is brought into contact with the second streaking area, and then a third zone of the plate is streaked. This process must be performed at least three or four times in order to be certain of obtaining individual colonies, rather than confluent growth, following incubation of the fresh plate.

BRIEF SUMMARY OF THE INVENTION

An object of the present invention is to provide a microorganism culture-transfer device having advantages over the known devices in the above respects.

According to a broad aspect of the present invention, there is provided a microorganism culture-transfer device comprising a manually-grippable handle having a culture contacting tip for contacting a culture and streaking same a plurality of times over a culture plate in order to dilute the culture for purposes of isolating individual colonies, characterized in that the handle is of a configuration non-circular in cross-section having a plurality of at least three longitudinally-extending linear surfaces projecting from the outer face of the handle defining at least three discrete rotational positions when held between two of the user's fingers and rotated about the longitudinal axis of the handle, by moving one of the fingers relative to the other, the culture-contacting tip being of a configuration such as to provide a different and distinct surface for contact with the culture medium in each of said discrete rotational positions of the handle.

The novel device constructed in accordance with the foregoing features provides a number of important advantages over the known devices briefly described above. Thus, when the known wire loop is used, it is necessary to heat and cool the wire loop between each streaking operation, there being typically four streaking operations to obtain the required colony dilution. When the disposable loop is used, a new loop must be brought to the culture medium for each streaking operation, and the previous loop discarded. Both cases involve not only significant time and effort, but also some chance of contaminating either the culture plate or the loop with foreign microorganisms, because of the many manipulations required and the duration that the culture plate is required to be open. Such time, effort, and chances of contamination are all considerably reduced with the present invention since the same device is used for all the streaking operations and is merely rotated a partial revolution (e.g. one-fourth revolution for performing four streaking operations) between each streaking operation.

Another important advantage, particularly when the disposable device is used, is that all the streaking operations require only one device rather than a number (e.g. four) required when using the known disposable loops.

The novel device may also be employed for inoculation from liquid medium to solid medium, from various solid surfaces, or for inoculation of mixed cultures, in a manner similar to that employed by presently existing devices.

The culture-contacting tip of the novel device may take a number of configurations, several of which are described below for the purposes of example. Thus, described below are tips having the configurations of a sphere, a disc, an annular ring, a clover leaf, and a plurality of radiating ribs, intersecting loops, or spheres.

The handle may be of polygonal cross-section (e.g. square), formed with a plurality of planar sides, the junctures between adjoining sides of the handle constituting the above-mentioned longitudinally-extending linear surfaces projecting from the outer face of the handle, such that each side defines one of the plurality of discrete rotational positions of the handle; alternatively, the handle may be formed with longitudinally-extending ribs constituting the above-mentioned longitudinally-extending linear surfaces projecting from the outer face of the handle and defining the discrete rotational positions. Markings may be provided on the handle to indicate a particular sequence of use, e.g. raised dots, or numbers, or different coloured markings for each side of the handle.

The device of the present invention may be constructed either as a reusable unit, wherein the culture-contacting tip may of metal, ceramic, wood, autoclavable plastic or the like; or it could be constructed as a one-time, disposable unit, wherein the device may be of plastic, wood or the like.

Further features and advantages of the device will be apparent from the description below.

BRIEF DESCRIPTION OF THE DRAWINGS

The invention is herein described, by way of example only, with reference to the accompanying drawings, wherein:

FIG. 1 is a three-dimensional view illustrating one form of microorganism culture-transfer device constructed in accordance with the present invention;

FIG. 2 illustrates how the device of FIG. 1 is used for transferring a culture by a plurality of streaking operations in order to isolate a single colony;

FIGS. 3-11 are fragmentary views illustrating other configurations of culture-transfer devices in accordance with the present invention; and FIG. 12 illustrates a still further device in accordance with the invention.

DESCRIPTION OF PREFERRED EMBODIMENTS

Figure 6:
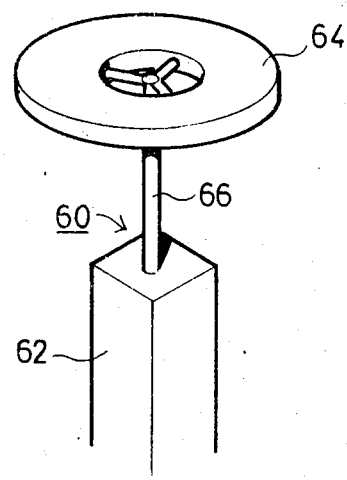

FIG. 1 illustrates a culture-transferring device 10 including a handle 12 at one end, and a culture-contacting tip 14 at the opposite end joined to the handle by a stem 16. In the embodiment of the invention illustrated in FIG. 1, handle 12 is of square cross-section, and the culture-contacting tip 14 is of spherical configuration, having a diameter, e.g., of 0.2-1.0 cm. When device 10 is constructed for reuse, it may be constructed of autoclavable material, such as polypropylene, polycarbonate, wood, ceramic, metal or the like, or a combination thereof. When device 10 is constructed for one-time use, it may be of plastic (e.g. polystyrene), wood or the like, presterilized by irradiation.

FIG. 2 illustrates the manner of using the device 10 in a plural-streaking operation in order to dilute a culture sufficiently for isolating individual colonies. The culture medium is in a Petri dish 20. In the dilution procedure, device 10 is used first to streak region 21 of the culture medium, and then regions 22, 23, 24, in that sequence, so that the culture in the final region 24 will be diluted several orders of magnitude with respect to the culture in the first region 21.

When device 10 is used in performing this sequence of streaking operations, its handle 12 is grasped by the user's fingers and is rotated above the longitudinal axis of the device one-fourth revolution between each streaking operation in order to provide a different surface for contact with the culture during each such streaking operation.

Thus, to produce the streaking operation in the first region 21, the user holds device 10 in one rotational position, brings the undersurface of tip 14 into contact with the colony of cells to be transferred, brings the same undersurface of tip 14 into contact with the culture medium 20 and performs the streaking operation in the first region 21. Then the user, while still holding the device proximally to the culture medium, rotates it one-fourth revolution about its longitudinal axis to present a different and distinct surface of tip 14 for contact with the culture medium 20, and performs the second streaking operation in region 22 of the culture medium. The device 10 is then rotated by the user another one-fourth revolution to present a third fresh surface of tip 14 for contact with the culture medium, and performs the third streaking operation in region 23; and then rotates the device another one-fourth revolution to present a fourth fresh surface of tip 14 for contact with the culture to perform the fourth streaking operation in region 24 of the culture medium.

The square cross-section of handle 12 greatly facilitates the rotation of handle 12, and thereby of tip 14, one-fourth revolution between each streaking operation, this rotation being effected by gripping the handle between the user's thumb and index finger and then shifting the thumb laterally with respect to the index finger. Preferably, the four faces of handle 12 are sequentially numbered "1-4", as shown by indicia 18 in FIG. 1, or provided with other indications to inform the user of the proper sequential rotation of the device.

FIGS. 3-11 illustrate further configurations of the culture contacting tip which may be used in substantially the same manner as described above with respect to the device of FIG. 1. In all these variations, the handle is illustrated as of square-cross-section, since such devices are typically used for performing four streaking operations. It will be appreciated, however, that the cross-section of the handle could include a different number of sides (e.g., three or five) if the device is to be used in a procedure involving three or five streaking operations, respectively.

Thus, the device illustrated in FIG. 3, and therein generally designated 30, includes a handle 32, a spherical culture-contacting tip 34, a stem 36, and indicia 38, all as described above with respect to device 10 illustrated i FIG. 1. The only difference in the device illustrated in FIG. 3 is that the spherical tip 34 is formed with two circular recesses 39 over its outer face dividing its outer face into four discrete surface sections for contact with the culture medium, each section being separated by a portion of he circular recess 39. Device 30 of FIG. 3 may be constructed for reuse, in which case the circuit tip 34 would be of metal for flame-sterilization or of wood for autoclaving; or it could be constructed for one-time use, in which case tip 34 would be of plastic, wood, ceramic or the like, sterile or sterilizable, e.g. by irradiation.

FIG. 4 illustrates a construction particularly useful when the device is for reuse. Thus, the device 40 also includes a handle 42, a spherical tip 44, and a stem 46, except in this case the spherical tip 44 is made of a mesh of metal wire to facilitate sterilization by flame before the device is to be used for performing the first streaking operation; its sterilization between streaking operations in the same isolation procedure is not required as when using the conventional metal loop.

FIG. 5 illustrates another device 50, also including a handle 52, a culture-contacting tip 54, and a stem 56, except in this case the culture-contacting tip 54 is in the shape of a circular disc fixed to the handle 52 perpendicularly to the longitudinal axis of the handle. That is, the planar axis through disc 54 is perpendicular to the longitudinal axis of handle 52. Device 50 illustrated in FIG. 5 is used in the same manner as described with respect to FIG. 2 since, in practice, only the annular equatorial portion of the spherical tip 14 in FIG. 1 is actually used, this portion being equivalent to the outer edge of disc 54 in FIG. 5.

FIG. 6 illustrates a still further variation wherein the culture-contacting tip, therein designated 54, is in the shape of an annular ring, equivalent to the outer portion of disc 54 in FIG. 5. As in FIG. 5, the plane of ring 64 in FIG. 6 is also fixed, via stem 66, to the handle 62 so as to extend perpendicularly to the longitudinal axis of the handle.

Figure 7:
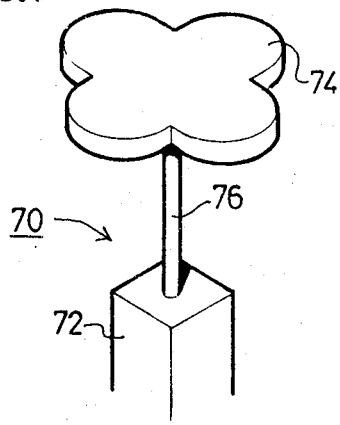

FIG. 7 illustrates a still further variation 70 wherein the culture-contacting tip 74 is in the configuration of a clover leaf having four sections, one for each of the four sides of the handle 72. The clover leaf tip in FIG. 7 is also secured, via stem 76, to extend perpendicularly to the longitudinal axis of handle 72 so as to provide a separate fresh surface for contact with the culture medium during each rotational position of the handle.

Figure 8:
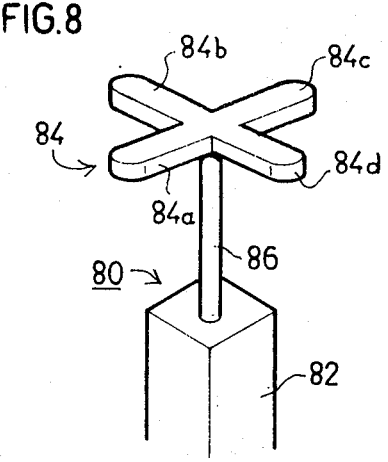

FIG. 8 illustrates a still further variation 80 wherein the culture-contacting tip 84 is constituted of a plurality of ribs 84a-84d joined together at their inner ends to handle 82, via stem 86, and radiating outwardly of the handle in a direction perpendicular to the longitudinal axis of the handle. Thus, the outer tip of each of the radiating ribs 84a-84d is positioned to contact the culture medium with each one-fourth rotation of the handle during the procedure described above with respect to FIG. 2.

Figure 9:
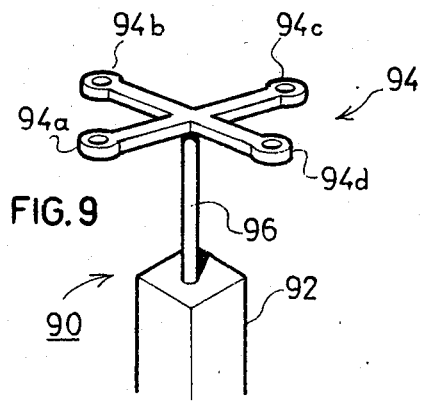

FIG. 9 illustrates a variation in the rib construction of FIG. 8, wherein the culture-contacting tip 94 secured to handle 92 of the device 90 by stem 96 is also formed with radiating ribs 94a-94d, but the outer tip of each rib is formed with a loop for contact with the culture medium.

Figure 10:
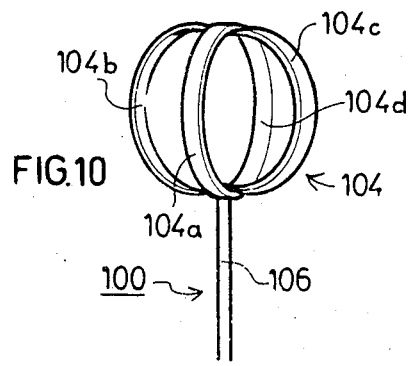

FIG. 10 illustrates a still further variation wherein the culture-contacting tip 104 at the end of stem 106 of the device 100 is in the configuration of two intersecting loops, thereby providing four semi-circular surface 104a-104d, each separate and distinct from the others, for contact with the culture medium during the four streaking operations.

Figure 11:
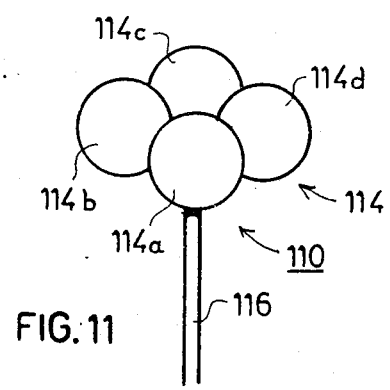

FIG. 11 illustrates a still further variation wherein the culture-contacting tip 114 carried at the end of stem 116 of the device 100 is in the configuration of four contiguous spheres 114a-114d, preferably joined together along the longitudinal axis of the device.

FIG. 12 illustrates a culture-transfer device comprising a manually-grippable handle having a spherical-type culture-contacting tip 124 at one end, and a conventional loop 127 at the opposite end. Thus, the spherical tip 124 may be of the same construction as tip 14 in FIG. 1 and is joined to the respective end of handle 122 by a stem 126. The conventional loop 127 is joined to the opposite end of handle by another stem 128. In this case, handle 122 is provided with a plurality of radiating ribs 122a-122d to define the plurality of discrete rotational positions of the handle when held by the user's fingers and rotated about the handle longitudinal axis. In the FIG. 12 arrangement, handle 122 is of X-cross-section, defining four radiating ribs 122a-122d, but it will be appreciated that the handle could include a different number of such ribs to define a different number of discrete positions of the culture-contacting tip 124.

Preferably, the device illustrated in FIG. 12 is made as a unitary device of plastic material, the X-section of the handle providing the additional advantage of permitting faster cooling after molding because of its increased outer surface area as compared to that of the polygonal configuration of the other embodiments.

The spherical tip 124, as well as the culture-contacting tips in the other described arrangements, may be provided with a roughened surface.

Many other variations, modifications and applications of the invention will be apparent.

What is claimed is:

1. A microorganism culture transfer device comprising a manually-grippable handle having a culture contacting tip at its two opposite ends for contacting a culture and streaking same a plurality of times over a culture plate in order to dilute the culture for purposes of isolating individual colonies, characterized in that said handle is of a configuration non-circular in cross-section having a plurality of at least three longitudinally-extending ribs constituting linear surfaces projecting from the outer face of the handle defining at least three discrete rotational positions when held between two of the use's fingers and rotated about the lingitudinal axis of the handle by moving one of said fingers relative to the other; and in that at least one of said culture-contacting tips is of a configuration such as to present a surface for contact with the culture when the handle is initially grasped by the user in any rotational position of the handle, and to provide a different and distinct but like surface around its circumference for contact with the culture in each of said discrete rotational positions of the handle.

2. The device according to claim 1, wherein said one culture-contacting tip is of spherical configuration.

3. The device according to claim 2, wherein the outer surface of said spherical culture-contacting tip is formed with a plurality of circular recesses over its outer face dividing it into discrete surface sections for contact with the culture.

4. The device according to claim 1, wherein said one culture-contacting tip is in the configuration of a circular disc fixed to the handle perpendicularly to the longitudinal axis of the handle.

5. The device according to claim 1, wherein said one culture-contacting tip is in the configuration of an annular ring fixed to the handle perpendicularly to the longitudinal axis of the handle.

6. The device according to claim 1, wherein said one culture-contacting tip is in the configuration of a clover leaf fixed to the handle perpendicularly to the longitudinal axis of the handle, which clover leaf has a separate section for each of said rotational positions of the handle.

7. The device according to claim 1, wherein said one culture-contacting tip is in the configuration of a plurality of ribs, one for each of said rotational positions of the handle, which ribs are joined together and to said handle at their inner ends and radiate outwardly of said handle in a direction perpendicularly to the longitudinal axis of the handle.

8. The device according to claim 1, wherein said one culture-contacting tip is in the configuration of a plurality of intersecting loops to provide a plurality of different and distinct surfaces for contact with the culture.

9. The device according to claim 1, wherein said one culture-contacting tip is in the configuration of a plurality of contiguous spheres joined together along the longitudinal axis of the device.

* * * * *